United States Patent [19]
Houkuwa

[11] Patent Number: 5,103,076
[45] Date of Patent: Apr. 7, 1992

[54] STRUCTURE OF DOUBLE STEAM OVEN

[76] Inventor: Mamoru Houkuwa, 4-15, Higashi Kashiwamachi, Matsuto-shi Ishikawa-ken, 924, Japan

[21] Appl. No.: 612,453

[22] Filed: Nov. 14, 1990

[51] Int. Cl.⁵ .......................... F22B 1/28; F24C 7/00
[52] U.S. Cl. .................................................. 219/401
[58] Field of Search ............... 219/401, 521, 385, 386; 392/374, 403, 405

[56] References Cited

U.S. PATENT DOCUMENTS

| | | | |
|---|---|---|---|
| 2,715,898 | 8/1955 | Michaelis | 219/401 |
| 3,604,895 | 9/1971 | MacKay | 219/401 |
| 4,460,822 | 7/1984 | Alden | 219/401 |
| 4,650,968 | 3/1987 | Williams | 219/401 |
| 4,722,268 | 2/1988 | Rightley | 219/401 |
| 4,897,525 | 1/1990 | Hirsch | 219/401 |
| 4,947,026 | 8/1990 | Groom | 219/401 |

FOREIGN PATENT DOCUMENTS 59-27228  8/1984  Japan .
60-4428   2/1985  Japan .

Primary Examiner—Teresa J. Walberg
Attorney, Agent, or Firm—Jones, Tullar & Cooper

[57] ABSTRACT

A double-walled steam oven is disclosed wherein an outer oven wall surrounds, and is spaced from an inner oven wall, the inner oven wall defining a heating or sterilization chamber. The heating chamber includes a rack or other support for receiving articles to be steam heated or sterilized. A hot water tank is provided at the bottom of the inner oven, where steam is generated by a suitable heater. The steam rises through the inner oven, and exits therefrom at the top wall thereof into the outer oven. The exiting steam is then forced downwardly around the exterior of the walls of the inner oven and exits from the outer oven near the bottom. Condensate formed on the outer wall of the outer oven drains down to the bottom of the oven into a return water tank, from which it flows back to the heater tank in the inner oven.

8 Claims, 4 Drawing Sheets

STRUCTURE OF DOUBLE STEAM OVEN

TECHNICAL FIELD

This invention relates to apparatus for heating, sterilizing and disinfecting food, seed beds, wood, culture media, and the like.

BACKGROUND OF THE INVENTION

At the present time, steam ovens are used to sterilize seed beds such as those used for example, in growing mushrooms. Such steam ovens have a single-walled structure which causes cooling in the chamber. Thus, external air adversely affects the temperature of the steam, with the result that the articles contained within the oven are sterilized unevenly. Furthermore, since the steam is used only once in such ovens, and the condensate is not recycled for reuse, a high-pressure bactericidal oven which does not utilize an exterior water supply cannot be used for long periods of treatment. On the other hand, in the case of a bactericidal oven used at atmospheric pressure where water can be supplied from an exterior source, long periods of treatment are possible but the cost of heating water is high.

SUMMARY OF THE INVENTION

It is an object of the present invention to provide an oven for use in heating, sterilization, and disinfecting of food, seed beds, wood and culture media such as that provided for use as seed beds for mushrooms and the like, wherein sterilization and heating can be provided with a relatively low heating cost, and wherein uniform treatment of the material can be obtained.

The oven of the present invention utilizes a double-walled structure to prevent uneven sterilization and to save on heating costs. An outer oven wall encloses and covers an inner oven wall, the outer wall serving to condense the steam into water and to return it to a steam generating area. As a result of this return flow, little water is lost in the process, and it is possible to use the oven structure for a long period of time without supplying additional water, thus reducing the heating cost. In addition, even when additional water is supplied during the operation of the device, so little additional water is required that there is a large savings in the heating cost compared to ovens currently in use.

When a high temperature bactericidal oven is required, a high pressure can be provided in the device of the present invention if the oven is provided with a pressure-proof structure and is equipped with a pressure adjustment valve in a steam exhaust port. Furthermore, even if only a part of the oven has a double structure, fuel efficiency improves. The heat source can be electricity, oil, gas, or even steam from a steam boiler. However, electricity is recommended because of its safety.

BRIEF DESCRIPTION OF THE DRAWINGS

The foregoing, and additional objects, features and advantages of the present invention will become apparent to those of skill in the art from a consideration of the following detailed description of a preferred embodiment thereof, taken in conjunction with the accompanying drawings, in which.

DESCRIPTION OF PREFERRED EMBODIMENTS

Figure 1:
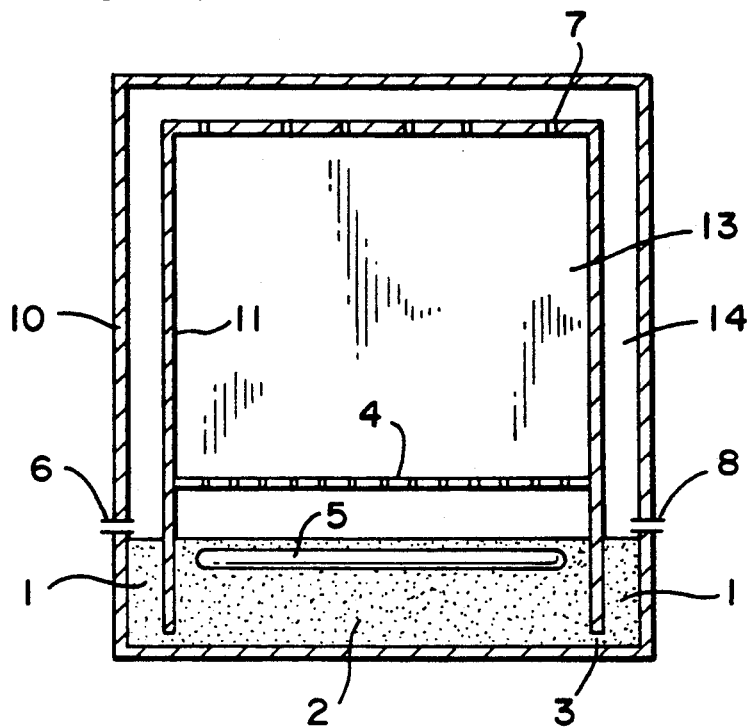
FIG. 1 is a cross-sectional view of a steam oven constructed in accordance with the present invention.

Turning now to a more detailed consideration of the drawings, there is illustrated in FIG. 1 a double-walled steam oven constructed in accordance with a first embodiment of the present invention. The oven includes a pair of hot water reservoirs 1 and 2 formed in the bottom of the oven. Reservoir 1 is an outside return tank located between the inner and outer walls of the oven while the reservoir 2 is a hot water heating tank formed within the inner wall of the oven. A water supply inlet 3 permits water from the return tank 1 to flow into the heating tank 2 to recycle the water after it has been condensed from the steam formed in the heating tank. A support 4 such as a drain board having a plurality of apertures is provided above the top surface of the water in heating tank 2 and serves to support the materials which are to be heated by steam. A heater 5 is located in the water contained in heating tank 2 and provides sufficient heat to convert the water into steam. Steam from heater 5 in the hot water tank passes through the drain board 4 and heats the articles supported on the drain board. The remaining steam passes upwardly through steam exit apertures 7 located in the top wall of the inner oven.

The outer oven is defined by an outer wall 10 spaced from and surrounding an inner wall 11. The inner wall covers the drain board 4 and the heating tank 2 and forms an inner oven 13. The outer oven is defined by the space 14 between walls 10 and 11. The steam which passes through aperture 7 into the outer oven 14 is cooled by the outer wall 10 and condenses, the condensed hot water draining downwardly to the hot water return tank 1. Air in the inner oven 13 and the outer oven 14 is evacuated by the steam generated in the hot water tank 2 and is let out of the oven by way of the steam exhaust port 6. A temperature controller (illustrated at 9 in FIG. 3) may be attached to the outer oven 14 for use in controlling the temperature of the heater 5 and thereby to control the amount of steam produced in the oven. Normally, only a small amount of steam will escape from the steam exhaust port 6.

Hot water in the hot water return tank 1 and cold water supplied from a feed water pipe 8 are mixed in the hot water tank 1 and the mixed water passes downwardly through the water supply inlet 3 to return to the hot water tank 2.

Figure 2:
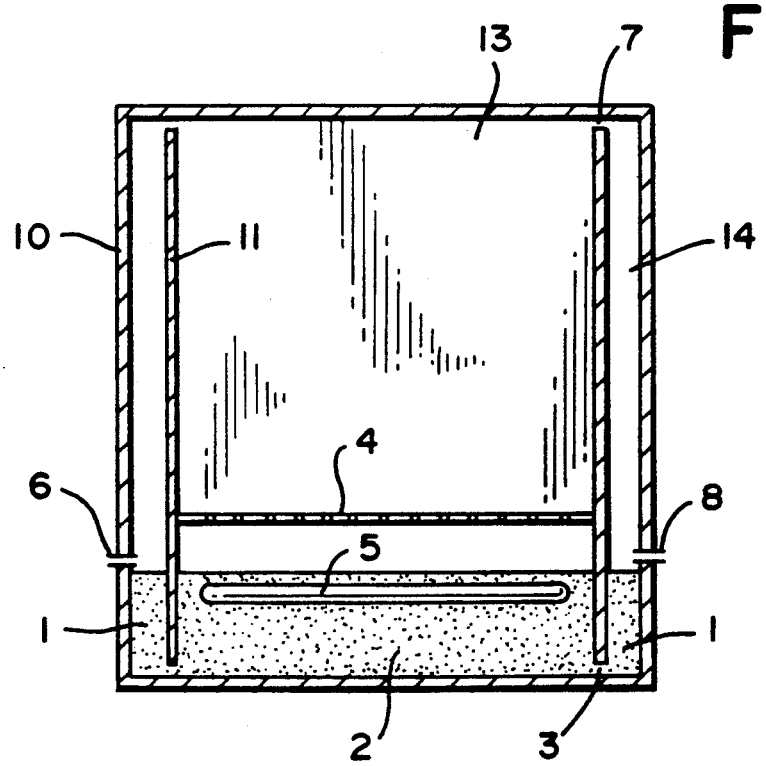
FIG. 2 is a cross-sectional view of a second embodiment of the oven of the present invention.

In a modified form of the invention, as illustrated in FIG. 2, the oven can be formed with double spaced walls 10 and 11 on the sides, but with only a single wall at the top. Thus, the inner oven walls terminate near the top of the outer oven wall and are spaced from the ceiling of the outer oven, with aperture 7 being located around the perimeter of the inner oven wall 11. Steam thus fills the inner chamber 13 and escapes therefrom through the perimeter apertures 7 into the outer oven chamber 14 in the manner described above with respect to FIG. 1.

Figure 3:
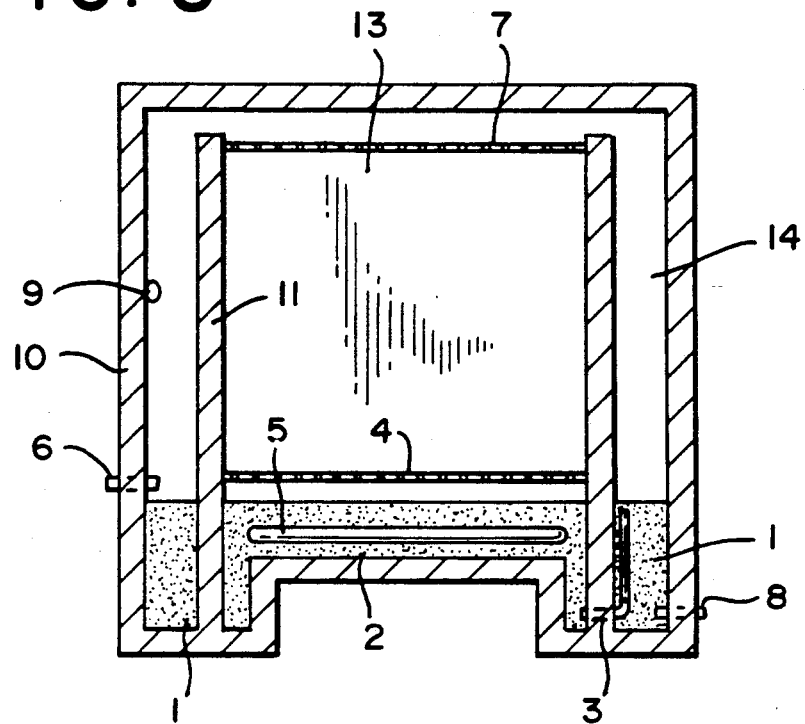
FIG. 3 is a cross-sectional view of a third embodiment of the oven of the present invention.
Figure 4:
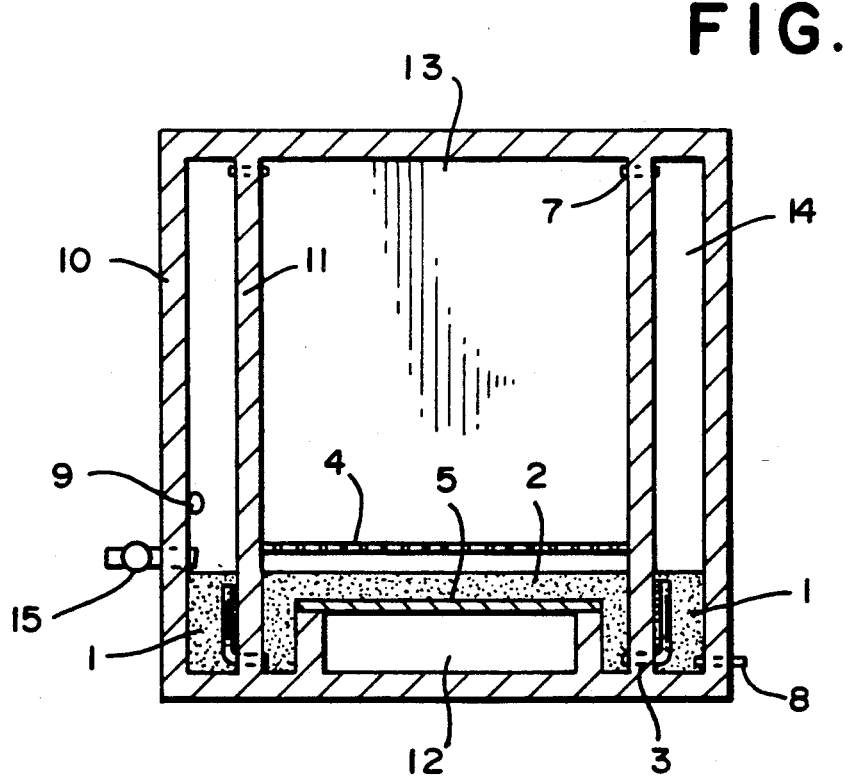
FIG. 4 is a cross-sectional view of a fourth embodiment of the present invention.

In the embodiment of FIG. 3, the water which is supplied by the feed water pipe 8 is supplied at the bottom of return tank 1 and the inner and outer tanks 1 and 2 are separated from each other by the wall 11 of the inner tank, except for the water supply inlet 3 which, in this case, is in the form of an inlet pipe having a vertical riser which extends toward the top of the tank 1. As illustrated in FIG. 4, a plurality of these standpipes may be provided to admit return water to the hot water tank 2.

In the embodiment of FIG. 3, the bottom wall of the tank is shaped to provide an upwardly extending chamber beneath the heater 5 to reduce the amount of water contained in the heating tank 2.

The heating source for heater 5 can be oil, gas or electricity. When using oil or gas, it is preferred that the oven be heated from the bottom of the tank 2, as indicated in FIG. 4 by the combustion chamber 12 spaced below a heater plate 5. The position of the heating plate 5 should be above the level of the water supply inlet 3 for effective generation of steam.

The steam exhaust port 6 preferably is located near the upper surface of the water in return tank 1 so that it can serve as an overflow for the oven. If it is desired to provide a pressurized oven, the outer oven 14 can be made pressure resistant in known manner, in which case the steam exhaust port 6 would be fitted with a pressure controller 15. This allows the oven to be used as a pressurized type steam oven.

Although not shown in FIGS. 1 to 4, the ceiling portion or top wall portion of the walls of the oven can serve as the access door to the interior of the oven chamber 13 in which the articles to be heated are placed. Alternatively, the access doors can be placed in the side walls of the oven. Articles in the inner chamber will be covered with steam and by reason of the double wall construction with the resulting exterior oven chamber 14 surrounding wall 11, the temperature within oven 13 will remain substantially even throughout so that articles placed at any desired location within the inner oven 13 will be sterilized or disinfected evenly. Since the steam which passes through the inner oven and enters the outer oven 14 is then condensed into hot water and returns to the hot water tank, very little additional water is required, thereby allowing operation of the oven over a relatively long period of time without the need for adding water from an exterior supply. Furthermore, by using a temperature controller in the outside oven, the amount of steam which is exhausted to the outside through exhaust port 6 can be reduced.

Figure 5:
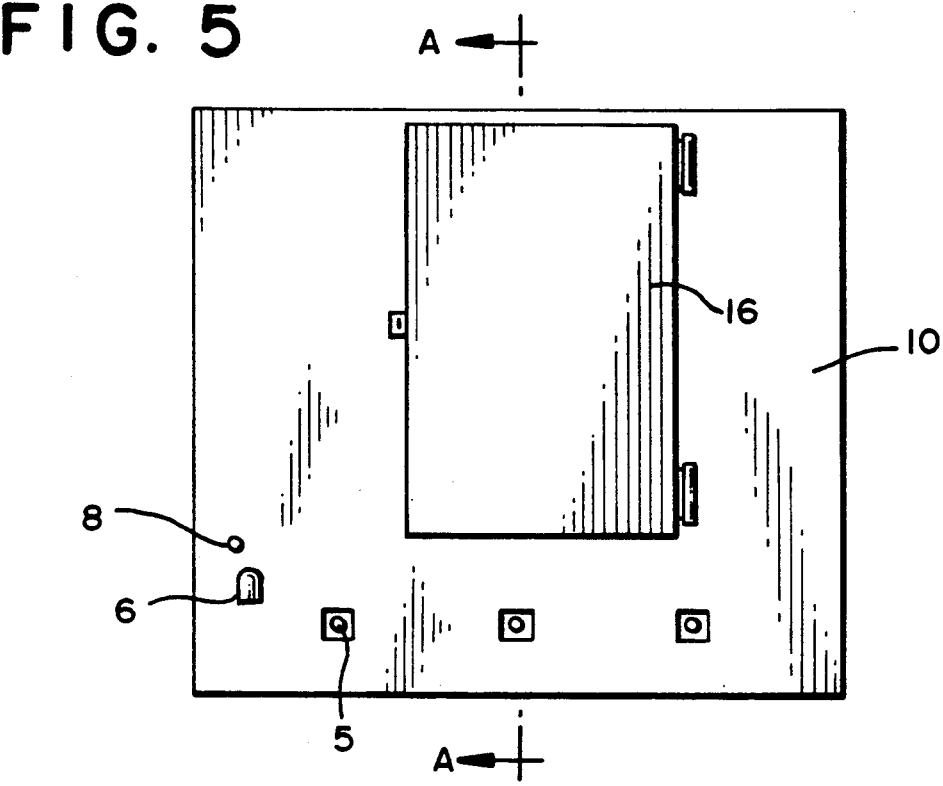
FIG. 5 is a front plan view of an oven constructed in accordance with the present invention.
Figure 6:
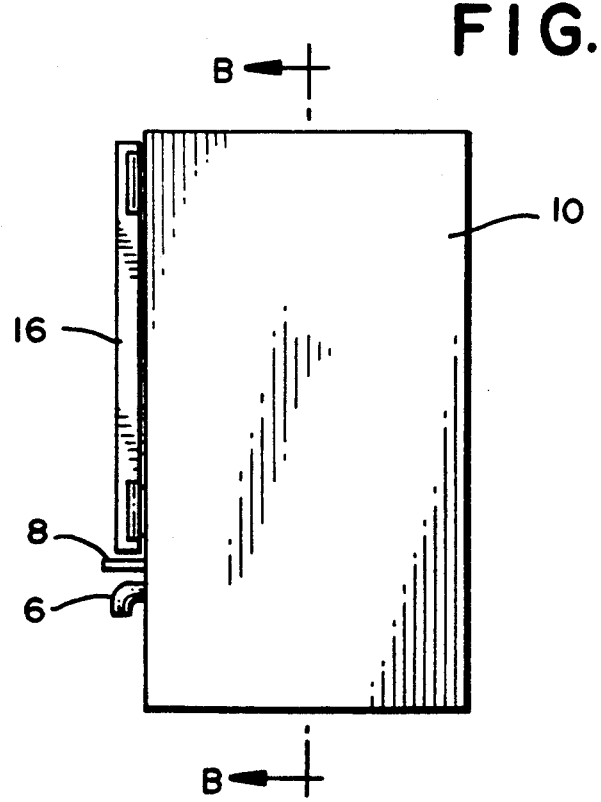
FIG. 6 is a side view of the oven of FIG. 5.

FIGS. 5 and 6 show the exterior configuration of the ovens illustrated in FIGS. 1 through 4, showing the location of a door 16 formed in the outer oven wall 10 amnd showing the location of suitable connections for the heater 5. Also shown in FIGS. 5 and 6 are the locations of the steam exhaust port 6 and the feed water pipe 8 for one configuration of the oven.

Figure 7:
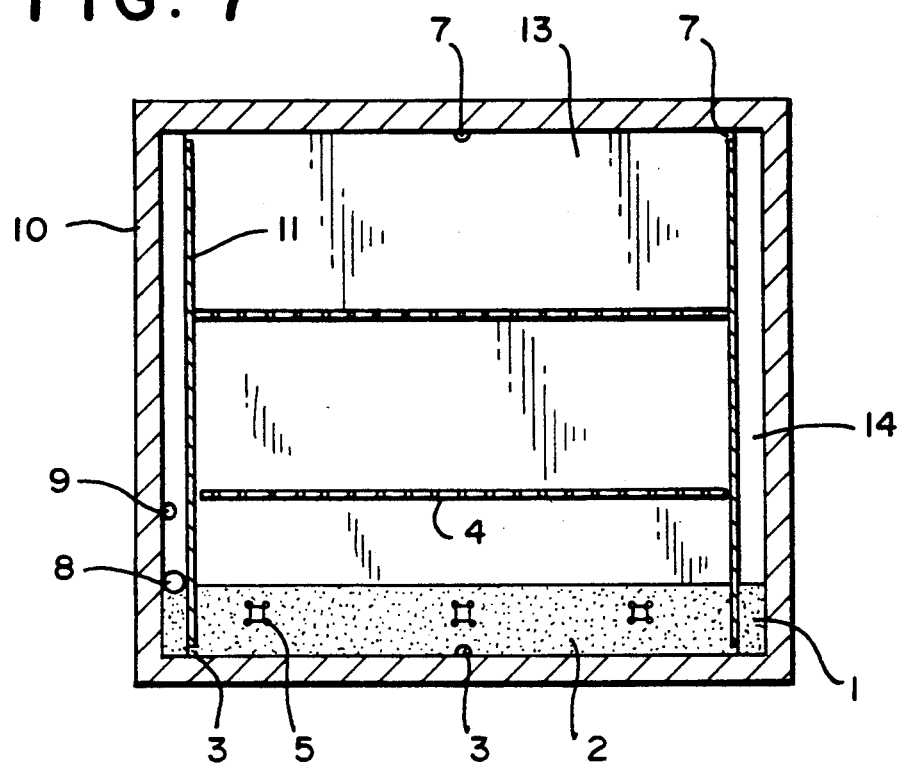
FIG. 7 is a cross-sectional view of a fifth embodiment of the invention, taken along line B—B if FIG. 6.
Figure 8:
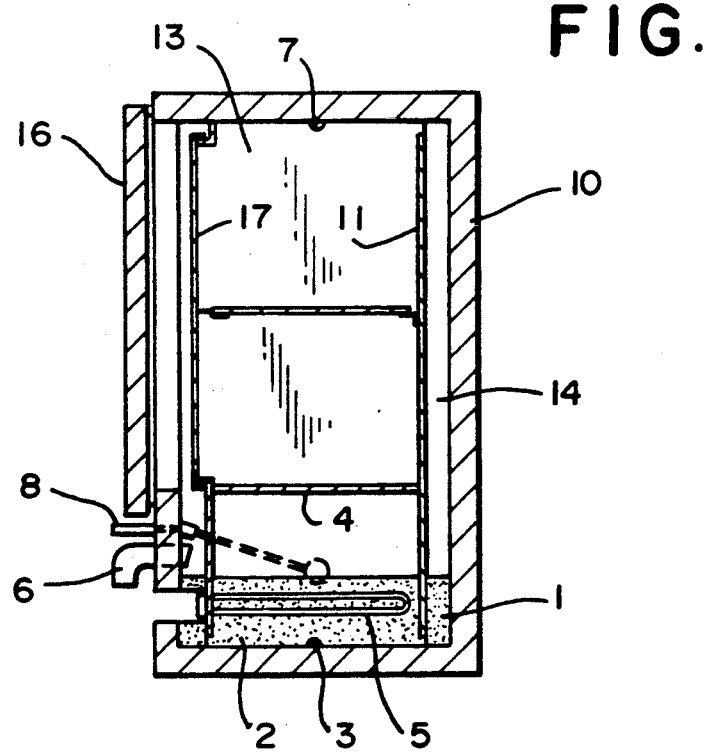
FIG. 8 is a cross-sectional view of the embodiment of FIG. 7 taken along line A—A of FIG. 5.

FIGS. 7 and 8 illustrated still another embodiment of the invention, FIG. 7 being a cross-sectional view taken along line B—B of FIGS. 6 in similar manner to FIGS. 1 through 4, and FIG. 8 being a cross-sectional view taken along line A—A of FIG. 5. In this embodiment, the inner oven is similar in structure to that of FIG. 2, and instead of a single drain board, two spaced drain boards are illustrated. Furthermore, in this embodiment, the heater 5 consists of three spaced heater electrodes connected to the exterior connections illustrated in FIG. 5. Furthermore, the feed water pipe 8 is illustrated as incorporating a level sensing mechanism for automatic replenishment of the water tank. Finally, the wall 11 of the inner oven is shown as incorporating an access door 17.

As a result of the foregoing structure, the heat efficiency of the double-walled oven becomes high, and less power or fuel is required than is needed for ovens currently in use. If an electric heater is used, the cost of using the oven is not much higher than the cost of oil or gas. Furthermore, with the use of an electric heater, noise can be eliminated and the risk of a fire is greatly decreased. Furthermore, maintenance is much easier and automatic operation using power in off-times when rates are reduced becomes possible.

Although the present invention has been described in terms of preferred embodiments, it will be understood that variations and modifications may be made without departing from the true spirit and scope thereof as set forth in the accompanying claims.

What is claimed is:

1. A double-walled steam oven comprising:
    an inner oven wall defining and enclosing an inner oven chamber;
    an outer oven wall surrounding said inner oven wall, said inner and outer oven walls defining therebetween an outer oven chamber, said inner and outer oven chambers being in fluid communication between adjacent upper portions thereof;
    a first water heating tank in a lower portion of said inner oven chamber;
    heater means immersed in said first water heating tank for converting water therein to steam, said steam rising to fill said inner oven chamber and flowing into said outer oven through said means providing fluid communication between said inner and outer ovens, said steam flowing downwardly from said fluid communication means through said outer oven chamber;
    a second water heating tank in a lower portion of said outer oven chamber for receiving condensate formed in said outer oven chamber by said steam flowing downwardly through said outer oven chamber;
    means provided in said inner oven wall adjacent a lower portion thereof for establishing liquid communication between said first and second water heating tanks to recycle condensate from said second to said first water heating tank; and
    exhaust port means located in said outer oven wall adjacent a lower portion thereof and located above the water level in said second water heating tank for permitting excess steam to escape from said outer oven chamber.

2. The double-walled steam oven of claim 1, further including means supplying make-up water to said second water heating tank.

3. The double-walled steam oven of claim 1, wherein said heater means is an electric heater.

4. The double-walled steam oven of claim 1, further including means providing fluid communication between upper portions of said inner and outer oven chambers to allow steam produced in said inner oven chamber to flow to said outer oven chamber.

5. The double-walled steam oven of claim 1, further including a pressure controller in said exhaust port means.

6. The double-walled steam oven of claim 2, further including means providing fluid communication between upper portions of said inner and outer oven chambers to allow steam produced in said inner oven chamber to flow to said outer oven chamber.

7. The double-walled steam oven of claim 6, further including a pressure controller in said exhaust port means.

8. The double-walled steam oven of claim 7, wherein said heater means is an electric heater.

* * * * *